US006051604A

United States Patent [19]
Fitzgerald

[11] Patent Number: 6,051,604
[45] Date of Patent: Apr. 18, 2000

[54] METHODS AND COMPOSITIONS FOR THE PREVENTION AND TREATMENT OF GASTROINTESTINAL DISORDERS

[75] Inventor: Jamesina Anne Fitzgerald, Hamilton, Ohio

[73] Assignee: The Proctor & Gamble Company, Cincinnati, Ohio

[21] Appl. No.: 08/569,033

[22] Filed: Dec. 7, 1995

[51] Int. Cl.[7] .......................... A01N 55/02; A01N 59/16; A01N 33/02; A61K 31/43
[52] U.S. Cl. ......................... 514/503; 424/653; 514/184; 514/199; 514/152
[58] Field of Search ........................... 424/653; 514/503, 514/184, 179, 152

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 418/110 |
| 5,221,664 | 6/1993 | Berkowitz et al. | 514/6 |
| 5,256,684 | 10/1993 | Marshall | 514/398 |

FOREIGN PATENT DOCUMENTS

| | | | |
|---|---|---|---|
| 962163 | 6/1950 | France | . |
| 63-174926 | 7/1988 | Japan | A61K 31/29 |
| WO 92/01457 | 2/1992 | WIPO | A61K 33/24 |
| WO 95/32720 | 12/1995 | WIPO | A61K 33/24 |

OTHER PUBLICATIONS

DuPont, H., et al., Symptomatic Treatment of Diarrhea With Bismuth Subsalicylate Among Students Attending a Mexican University, Gastroenterology, vol. 73, (1977), pp. 715–718.
DuPont, H., "Enteropathogenic Organisms: New Etiologic Agents and Concepts of Disease", Medical Clinics of North America, vol. 62, No. 5 (1978), pp. 945–960.
Wolfe, M., "The Treatment of Intestinal Protozoan Infections", Medical Clinics of North America, vol. 56, No. 3 (1982), pp. 707–720.
Journal of the American Medical Association, "Travelers' Diarrhea", vol 253, No. 18 (1985) pp. 2700–2704.
DuPont, L. "Nonfluid Therapy and Selected Chemoprophylaxis of Acute Diarrhea", The American Journal of Medicine, vol. 78, Suppl. 6B (1985), pp. 81–90.
Johnson, P., et al., "Comparison of Loperamide With Bismuth Subsalicylate for the Treatment of Acute Traveler's Diarrhea", The Journal of the American Medical Association, vol. 255, No. 6 (1986), pp. 757–760.
Steffen, R., "Anerkannte Prinzipien zur Prophylaxe und Therapie der Reisediarrhoe", Schweiz. med. Wschr. 116, Nr. 20 (1986), pp. 670–673 (translation provided).
DuPont, H., et al., "Prevention of Travelers' Diarrhea By the Tablet Formulation of Bismuth Subsalicylate", The Journal of the American Medical Association, vol. 257, No. 10 (1987), pp. 1347–1350.
White, N., "Drug Treatment and Prevention of Malaria", European Journal of Clinical Pharmacology, vol. 34 (1988), pp. 1–14.

D'Alessandro, A., "Amebiasis Then", American Journal of Tropical Medicine and Hygiene, vol. 41, No. 3, Suppl. (1989), pp. 38–39.
Steffen, R., "Worldwide Efficacy of Bismuth Subsalicylate in the Treatment of Travelers' Diarrhea", Reviews of Infectious Diseases, vol. 12, Suppl. 1 (1990), pp. S80–S86.
Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.
Wolfe, M., "Acute Diarrhea Associated With Travel", The American Journal of Medicine, vol. 88, Suppl. 6A (1990), pp. 34S–37S.
Qadri, S.M.H., "Infectious Diarrhea: Managing a Misery that is Still Worldwide", Postgraduate Medicine, vol. 88, No. 5 (1990), pp. 169–184).
Farthing, M.J.G., et al., "Treatment and Prevention of Travellers' Diarrhoea", Gastroenterology International, vol. 5, No. 3 (1992), pp. 162–175.
Zinsser Microbiology, 20th ed., Appleton & Lange (1992), pp. 1161–1173.
Arduino, R., et al., "Travellers' Diarrhoea", Bailliere's Clinical Gastroenterology, vol. 7, No. 2 (1993), pp. 365–385.
Chak, A., et al., "Traveler's Diarrhea", Gastroenterology Clinics of North America, vol. 22, No. 3 (1993), pp. 549–561.
American Health Consultants, "Cryptosporidiosis in Milwaukee", vol. 12, No. 15 (1993), pp. 113–115.
Weber, R., et al., "Disseminated Microsporidiosis Due to *Encephalitozoon hellem:* Pulmonary Colonization Microhematuria, and Mild Conjunctivitis in a Patient with AIDS", Clinical Infectious Diseases, vol. 17 (1993), pp. 415–419.
Weber, R., et al., "Disseminated Microsporidiosis Due to *Encephalitozoon Hellem:* Pulmonary Colonization Microhematuria, and Mild Conjunctivitis in a Patient with AIDS", Clinical Infectious Diseases, vol. 17 (1993), pp. 415–419.
Kuhls, T., "Protozoal Infections of the Intestinal Tract in Children", Advances in Pediatric Diseases, vol. 8 (1993), pp. 177–202.
Scott, D., et al., "Treatment of Gastrointestinal Infections", Bailliere's Clinical Gastroenterology, vol. 7, No. 2 (1993), pp. 477–499.
Martindale, The Extra Pharmacopoeia, "Gastro–intestinal Agents", Thirtieth Ed., The Pharmaceutical Press (1993), p. 872.

(List continued on next page.)

*Primary Examiner*—Russell Travers
*Attorney, Agent, or Firm*—Kirsten K. Stone; Betty J. Zea

[57] ABSTRACT

The subject invention encompasses methods for prevention and treatment of a human or lower animal subject having a gastrointestinal disorder caused or mediated by one or more intestinal helminths comprising administering to the subject bismuth and one or more antimicrobials. The subject invention also encompasses compositions comprising bismuth and one or more antimicrobials for the prevention and treatment of a human or lower animal subject having a gastrointestinal disorder caused or mediated by one or more intestinal helminths.

14 Claims, No Drawings

OTHER PUBLICATIONS

Health, "Are Milwaukee–Type Parasites Floating in My Drinking Water?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp. 568–569.

Upcroft, P., "Multiple Drug Resistance in the Pathogenic Protozoa", Acta Tropica, vol. 56 (1994), pp. 195–212.

Herwaldt, B., et al., "Infections with Intestinal Parasites in Peace Corps Volunteers in Guatemala", Journal of Clinical Microbiology (1994), pp. 1376–1378.

Physicians' Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

Chevalier, C., et al., "Bilan Des Antiparasitaires A Usage Veterinaire: Antihelminthiques, Anticoccidiens, Antifongiques, Ectoparasiticides" (translation attached), Laboratory of Therapeutic Chemistry, College of Pharmacy, 37042 Tours Cedex, pp. 624–630.

Cavier, R., "Etude des propriérés parasiticides de quelques complexes bismuthiques de l'oxy–8 quinoléine", Annales pharmaceutiques francaises, 1973, 31, No. 4, pp. 173–178 (translation attached).

Pitlik, S., et al., "Cryptosporidial Cholecystitis", The New England Journal of Medicine, vol. 308, No. 16 (Apr. 21, 1983), p. 967.

Than, U Pe, et al., "The Alkaloids of Holarrhena Antidysenterica", Union of Burma Journal of Science and Technology, vol. 2, Dec. 1969, pp. 423–436.

Willard, F. L., et al., "Survey of Chemical Compounds Tested In Vitro Against Rumen Protozoa for Possible Control of Bloat", Applied Microbiology, vol. 15, No. 5, Sep. 1967, pp. 1014–1019.

Chevalier, C., et al., "Bilan Des Antiparasitaires A Usage Veterinaire: Antihelminthiques, Anticoccidiens, Antifongiques, Ectoparasiticides"(translation attached), Laboratory of Therapeutic Chemistry, College of Pharmacy, 37042 Tours Cedex, pp. 624–30.

Du Pont et al JAMA vol. 257, #10 1987.

Wolf, 1982, Medical Class of WA., vol. 56 (3) pp. 707–720.

Wolf, 1990 The American J. of Medicine vol. 88 pp. 34–38.

METHODS AND COMPOSITIONS FOR THE PREVENTION AND TREATMENT OF GASTROINTESTINAL DISORDERS

BACKGROUND OF THE INVENTION

While many industrialized countries have come to regard infection by intestinal helminths as a problem of impoverished developing countries, this is far from true. The incidence of gastrointestinal infection by parasitic intestinal helminths continues to present a serious health concern. The World Health Organization and other authorities estimate that well over two billion of the population are infected annually with intestinal helminths. *Manual Of Clinical Microbiology*, Sixth Edition, 1141–1142. Worldwide, five hundred to eight hundred million are estimated to be infected with *Trichuris trichiura*, and nine hundred million with hookworm. Id. Treatment of helminth infections has had modest success due to the complexity of the parasitic life cycles of the organisms i.e., egg, first-stage larva, second-stage larva, third-stage larva, free-form, etc. In addition, an increasing display of resistance to commonly used antihelminthic agents further hinders the likelihood of successful treatment of helminth infections. Therefore, the need for effective antihelminthic therapies continues to grow.

It has been discovered by the present invention that the administration of bismuth salts and one or more antimicrobials may be effective for the prevention and/or treatment of gastrointestinal disorders caused or mediated by one or more intestinal helminths. Thus, an object of the present invention is to provide a safe and effective compositions and methods of preventing and/or treating gastrointestinal disorders caused or mediated by intestinal helminths. A further object of the invention is to provide such a method comprising the administration of bismuth and one or more antimicrobials.

These and other objects of the present invention will become readily apparent from the detailed description which follows.

SUMMARY OF THE INVENTION

The present invention relates to a method for treatment of a human or lower animal subject having a gastrointestinal disorder caused or mediated by one or more intestinal helminths comprising administering to the subject from about 50 milligrams to about 5000 milligrams of bismuth, per day, for from about 1 to 56 days; and from about 100 milligrams to about 10,000 milligrams of each of one or more antimicrobials, per day, for from about 1 to about 21 days.

The present invention also relates to a method of prevention in a human or lower animal for a gastrointestinal disorder caused or mediated by one or more intestinal helminths comprising administering to the subject from about 50 milligrams to about 5000 milligrams of bismuth, per day, for from about 1 to 21 days; and from about 100 milligrams to about 10,000 milligrams of each of one or more antimicrobials, per day, for from about 1 to about 14 days.

DETAILED DESCRIPTION OF THE INVENTION

The methods of the present invention comprise the prevention and/or treatment of gastrointestinal disorder caused or mediated by one or more intestinal helminths. Such gastrointestinal disorders are prevented and/or treated by the administration of bismuth and one or more antimicrobials. The components of the present invention are more fully defined below.

Gastrointestinal Disorder

The term "gastrointestinal disorder", as used herein, encompasses any infection, disease or other disorder of body, typically the upper and/or lower gastrointestinal tract, caused or mediated by one or more intestinal helminths. Such disorders include one or more of the following conditions: diarrhea, abdominal pain and/or cramping, epigastric fullness, constipation, blood and/or mucus present in feces, fever, vomiting, gastroenteritis, weight loss, anemia, malaise, pallor, anal pruritus, and any other condition commonly associated with infection by intestinal helminths. Severe infections may even result in dangerous migrations of infection to ectopic sites such as the liver, lungs, etc. or even death.

In immunocompromised subjects and children, gastrointestinal disorders caused or mediated by intestinal helminths may be more severe and life threatening than the common disorders listed above. Therefore, the term "gastrointestinal disorder" also includes any condition commonly associated with intestinal helminths in immunocompromised subjects and children, including but not limited to, bloody diarrhea, extreme constipation, irritability, extreme pruritus, wasting, listlessness, bowel obstruction, and retardation of development.

Intestinal Helminths

Intestinal helminths, commonly referred to as worms, are multi-cellular parasites which have been implicated in intestinal disease. The term "intestinal helminths", as used herein, refers to helminths of the following medically important groups: Nematodes, Trematodes, and Cestodes. These organisms are fully described in *Zinsser Microbiology*, 20th Edition, 1195–1215, (1992) and *Manual of Clinical Microbiology*, Sixth Edition, 1141–1144, and 1229–1243, (1995), both of which are incorporated herein by reference.

Nematodes (or roundworms) include *Trichinella spiralis, Enterobius vermicularis* (pinworm), *Ascaris lumbricoides, Trichuris trichiura* (whipworm), *Capillaria philippinensis, Ancylcolostoma duodenale* (common hookworm), *Necator americanus* (American hookworm), and Trichostrongylus (species such as *Strongyloides stercoralis* (threadworm). Trematodes (fluke worms) include *Fasciolopsis buski, Heterophyes heterophyes, Metagoniumus yokogawai*, and *Nanophyetus salmincola*. Cestodes (or tapeworms) include *Diphyllobothrium latum, Taenia saginata, Taenia solium*, and *Hymenolepis nana*.

Preferred intestinal helminths are *Enterobius vermicularis, Ancylostoma duodenale, Trichuris trichiura, Fasciolopsis buski*, Trichostrongylus species, *Taenia saginata*, and combinations thereof. Most preferred parasitic protozoa are *Enterobius vermicularis, Ancylostoma duodenale, Trichuris trichiura*, and combinations thereof.

Diagnosis of gastrointestinal disorders caused or mediated by intestinal helminths may be accomplished by any method commonly used in the medical community. Such methods are fully described in *Zinsser Microbiology*, and *Manual of Clinical Microbiology*, as referenced above.

Bismuth

The methods of treatment and/or prevention in the present invention involve administration of bismuth. As used herein, the quantity of bismuth is by weight of elemental bismuth.

The preferred duration of bismuth administration will vary according to the specific gastrointestinal disorder to be treated and the physical condition of the subject being treated. In general, as a method of treatment, bismuth may be administered in an amount of from about 50 milligrams to about 5000 milligrams, and preferably from about 50 milligrams to about 2500 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 5000 milligrams, and preferably from about 50 milligrams to about 2500 milligrams, per day, for from about 1 to about 21 days, and preferably for from about 1 to about 14 days. In a method of prevention, bismuth may be administered prior to potential exposure to intestinal helminths. Such administration of bismuth may vary depending on the likelihood of intestinal helminth exposure and condition of the subject and may be commenced at any time deemed beneficial by the medical community including from about 1 to about 7 days, from about 2 to about 5 days, and from about 3 to about 4 days, prior to potential exposure.

In the present invention, the term "bismuth", as used herein, includes bismuth in the form of a pharmaceutically-acceptable salt, bismuth in the form of an organic or other complex which contains bismuth as an active ingredient, and mixtures thereof. Such organic complexes include 2,2'-spirobi[1,32-benzodoxabismole]. Preferably, bismuth is administered in the present methods as a pharmaceutically-acceptable salt. Such bismuth salts include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgalate (by The Parthenon Co., Inc.); and Pepto-Bismol®, containing bismuth subsalicylate (by The Procter & Gamble Company).

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally.

Antimicrobial

The present invention also include administration of a safe and effective amount of one or more antimicrobials, per day. As used herein, the term "antimicrobial(s)" refers to one or more antimicrobials.

Typically, according to the present methods for prevention and treatment, each of the one or more antimicrobials is administered at a level of from about 100 milligrams to about 10,000 milligrams, per day, for from about 1 to about 28 days. Preferably, each of the one or more antimicrobials is administered at a level of from about 100 milligrams to about 8000 milligrams per day, and more preferably at from about 100 milligrams to about 5000 milligrams per day. It is also preferred that each of the antimicrobials is administered for from about 1 to about 7 to 10 days, more preferably for from about 1 to about 14 days, and most preferably for from about 1 to about 21 days. In the methods for prevention, it is further preferred that each of the one or more antimicrobials is administered for from about 1 to about 14 days, and preferably for from about 1 to about 7 to 10 days.

The specific dosage of antimicrobial(s) to be administered, as well as the duration of antimicrobial(s) treatment, are mutually dependent, and will also depend upon such factors as the specific antimicrobial used, the number of antimicrobials used in the treatment, the resistance pattern of the infecting organism to the antimicrobial used, the ability of the antimicrobial to reach minimum inhibitory concentrations at the site of the infection, the nature and extent of other infections (if any), the personal attributes of the subject, compliance with the treatment regimen, and the presence and severity of any side effects of the treatment. Therefore, in the case of prevention or treatment with more than one antimicrobial, the duration of administration should depend on the type of antimicrobial rather than the administration of the antimicrobials for the same number of days.

A wide variety of antimicrobials are useful in this invention. As used herein, the term "antimicrobial" refers to any naturally-occurring, synthetic or semisynthetic compound or composition or mixture thereof, which is safe for human use as used in the methods of this invention, and is effective in killing or substantially inhibiting the intestinal helminths when used in the methods of this invention. Antihelminthic agents, antiprotozoal agents, antiparasitic agents and antibiotics are among the preferred antimicrobials useful herein.

Antihelminthic agents suitable for use in the present invention include thiabendazole, mebendazole, albendazole, quinacrine hydrochloride, niclosamide, pyrantel pamoate, tetramisole, levamisole, bephenium, and praziquantel.

Antiprotozoal and antiparasitic agents suitable for use in the present invention include any of the agents recognized in the medical community as acceptable for treating protozoal infection. Such antiprotozoal and antiparasitic agents include atovaquone, chloroquine phosphate, quinacrine hydrochloride, iodoquinol, pyrimethamine, and mefloquine hydrochloride.

Antibiotics can be generally classified by chemical composition, into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin and amoxycillin; the polypeptides such as bacitracin and polymyxin; the tetracyclines such as tetracycline, chlortetracycline, oxytetracycline and doxycycline; the cephalosporins such as cephalexin and cephalothin; quinolones such as ciprofloxacin, norfloxacin and ofloxacin; and such miscellaneous antibiotics as trimethoprim, sulfamethoxazole and the combination thereof, and chloramphenicol. These antibiotics can generally be said to function in one of four ways: inhibition of cell wall synthesis, alteration of cell wall permeability, inhibition of protein synthesis or inhibition of nucleic acid synthesis.

Other antimicrobials useful herein include the sulfonamides; nitrofurans, such nitrofurazon, nitrofurantoin, and furozolidone; metronidazole, tinidazole, and nimorazole. Antimicrobials among those useful herein are described in *Remington's Pharmaceutical Sciences,* 18th Edition, pp. 1173–1232 (1990), which is incorporated herein by reference.

While any of these antimicrobials may be used, mebendazole, thiobendazole, praziquantel, and niclosamide are among the preferred antimicrobials for use in the present invention.

As stated above, the specific preferred quantity of antimicrobial and duration of treatment used in the methods of this invention will, in addition to other factors, depend upon the particular antimicrobial used and its pharmacology. In general, though, antihelminthic agents are preferably administered as follows: niclosamide at about 0.5 grams to 2 grams per day, praziquantel at about 0.5 grams to 10 grams per day, pyrantel pamoate at about 0.1 grams to 1 gram per day, thiabendazole at about 0.25 grams to 3 grams per day, and mebendazole at about 100 milligrams to 200 milligrams per day. The tetracyclines are preferably administered at a level of from about 100 milligrams to about 2,000 milligrams per day. Macrolides (such as erytiromycin) are preferably administered at a level of from about 1,000 milligrams to about 4,000 milligrams per day. Penicillins are preferably administered at a level of from about 500 milligrams to about 3,000 milligrams per day. The aminoglycosides (such as neomycin) are preferably administered at a level of from about 100 milligrams to about 8,000 milligrams per day. Nitrofurans (such as nitrofurantoin) are administered preferably at levels of from about 100 milligrams to about 800 milligrams per day. Preferably, metronidazole is administered at a level of from about 375 or 500 to about 2,000 milligrams per day. Preferably, atovaquone is administered at a level of from about 750 to about 2250 milligrams, per day.

The specific method of administering the antimicrobial, according to the processes of this invention, may depend upon such factors as the particular antimicrobial(s) used, the site of infection, the amount of antimicrobial(s) to be administered per day, the presence of any adverse side effects, and the interactions (if any) between the antimicrobial(s) and the bismuth. Thus, the antimicrobial(s) may be administered under the process of this invention by single daily doses, or by administration in two, three, four, or more doses per day.

Bismuth/Antimicrobial Compositions

The present invention also provides compositions for the treatment of gastrointestinal disorders comprising a safe and effective amount of bismuth and a safe and effective amount of one or more antimicrobials. Typically, these compositions comprise a safe and effective amount one or more antimicrobials; a safe and effective amount of bismuth; and any pharmaceutically-acceptable carrier materials; wherein the safe and effective amount of the one or more antimicrobials and the bismuth is effective for preventing and/or treating a gastrointestinal disorder caused or mediated by one or more intestinal helminths.

A preferred composition comprises:
(a) from about 50 milligrams to about 5,000 milligrams of bismuth; and
(b) from about 100 milligrams to about 10,000 milligrams of each of one or more antimicrobials.

Preferably, the bismuth salt is present at a level of from about 50 milligrams to about 2500 milligrams. Also, preferably each of the one or more antimicrobials is present at a level of from about 100 milligrams to about 8000 milligrams.

The compositions of the present invention may contain optional components which affect the physical and therapeutic characteristics of the present compositions. In particular, a variety of pharmaceutically-acceptable carriers and excipients may be included, depending upon the particular dosage form to be used. Various oral dosage forms can be used, including such solid forms as tablets, capsules, granules and bulk powders. Tablets can be compressed, tablet triturates, enteric-coated, sugar coated, film-coated or multiple compressed, containing suitable binders, lubricants, diluents, disintegrating agents, coloring agents, flavoring agents, flow-inducing agents and melting agents.

Liquid oral dosage forms include aqueous solutions, emulsions, suspensions, solutions, and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents.

Specific examples of pharmaceutically-acceptable carriers and excipients that may be used to formulate oral dosage forms of the present invention are described in U. S. Pat. No. 3,903,297, Robert, issued Sep. 2, 1975, incorporated by reference herein. Techniques and compositions for making dosage forms useful herein are described in the following references, all incorporated by reference herein: 7 *Modem Pharmaceutics*, Chapters 9 and 10 (Banker and Rhodes, editors, 1979); Lieberman, et al., *Pharmaceutical Dosage Forms: Tablets* (1981); and Ansel et al., *Pharmaceutical Dosage Forms and Drug Delivery Systems*, Fifth Edition, 134–254, (1990).

The compositions of this invention may be used according to the methods of this invention by administering the composition from 1 to 7 times per day, and preferably from 1 to 4 times per day; for from 1 to 21 days, preferably for from about 1 to about 14 days. The specific frequency of administration will depend upon such factors as the specific bismuth compound or composition and antimicrobial(s) used, the levels at which the components are incorporated in the composition, the nature and severity of the condition to be treated, and the nature of any concurrent therapy, if any.

Administration

The present invention comprises methods wherein the administration of bismuth and the administration of one or more antimicrobials are performed simultaneously (beginning and ending on the same day), concurrently (overlapping), or consecutively (sequential, but wherein the course of the treatment is substantially continuous). Preferably, the step of administering the antimicrobial(s) is not commenced prior to commencing the step of administering bismuth.

As used herein, the term "administering" refers to any method which, in sound medical practice delivers the compounds or compositions used in this invention to the subject to be treated in such a manner so as to be effective in the treatment of the gastrointestinal disorder. Preferably, the bismuth is administered orally. Also preferably, the antimicrobial(s) is administered either orally, intravenously, or any other method which effects systemic distribution, or local distribution to the site of the gastrointestinal disorder, of the antimicrobial(s) in the subject. Oral ingestion of the antimicrobial(s) is a preferred method of administering the antimicrobial(s) in the methods of this invention.

The following non-limiting examples illustrate the methods and uses of the present invention.

EXAMPLE I

A South African farmer enters a health clinic in an extremely weakened condition with sallow skin and a tender abdomen, describing periods of alternating diarrhea and constipation. Fecal bacterial isolates fail to identify the offending pathogen. Direct wet mount examination of the fecal specimens reveals the presence of thin shelled eggs (40–60 m) which confirms the diagnosis of *Ancylostoma duodenale*. Following the diagnosis, the patient is treated by administering a composition containing bismuth subsalicylate, sold by The Procter & Gamble Company under the name "Pepto-Bismol®". The composition, in liquid form, is administered four times daily in equal doses delivering approximately 2500 milligrams of bismuth per day, for 21 days. Mebendazole chewable tablets (100 milligrams per tablet) are concurrently administered twice daily for the first 3 days, delivering a total of 200 milligrams of mebendazole per day. After the completion of this regimen, fecal samples from the subject are analyzed again, finding no trace of helminthic infection. The patient remains asymptomatic, and another fecal analysis performed 5 months later is normal.

In the above example, tripotassium dicitrato bismuthate, bismuth tartrate, bismuth citrate, and bismuth subnitrate are substituted, respectively, for bismuth subsalicylate, with substantially similar results.

EXAMPLE II

A five-year-old child, from an indigent Appalachian family, is suffering from nausea, vomiting, and mucous diarrhea. Analysis of fecal specimens reveals the presence of barrel shaped eggs (20–50 m in size, golden brown in color, and having a transparent prominence or polar plug at each end), characteristic of *Trichuris trichiura*. The infection is diagnosed and treated by concurrent administration of 500 milligrams of thiabendazole in 5 milliliters of oral suspension and 100 milligrams of mebendazole in a chewable tablet daily for the first 2 successive days. After two days (commencing on the third day) approximately 400 milligrams of bismuth in the form of bismuth subcitrate ("DeNol" sold by Brocades), is administered in four equal doses daily for about 28 days. Thereafter, fecal samples from the subject are analyzed again, finding no trace of helminthic infection.

In the above example, albendazole, quinacrine hydrochloride, niclosamide, pyrantel pamoate, tetramisole, levamisole, praziquantel, atovaquone, chloroquine phosphate, iodoquinol, penicillin, erythromycin, nitrofuran, and tetracyline are substituted, respectively, for thiabendazole or mebendazole, with substantially similar results. In addition, either antibiotic can be eliminated from the regimen (e.g., due to hypersensitivity) and maintain therapeutic efficacy. Bismuth citrate, bismuth tartrate, bismuth aluminate, bismuth subgalate, bismuth subsalicylate, and tripotassium dicitrato bismuthate are substituted, respectively, for bismuth subcitrate, with substantially similar results.

EXAMPLE III

Eight children in a kindergarten class of twelve students have been diagnosed with pinworms. The parents of the four uninfected children solicit help from the student health service to prevent their children from becoming infected with *Enterobius vermicularis*. Clinical evaluation of the four children confirms that they had not been infected. The children are given approximately 400 milligrams of bismuth, in the form of bismuth subgalate (Devrom®, sold by The Parthenon Company, Inc.), in four equal doses daily, and 50 milligrams of pyrantel pamoate daily in 1 milliliter of oral suspension for about 14 days. The four children remain asymptomatic. Fecal samples from all children of the kindergarten class are analyzed and no evidence of pinworm infection is found.

What is claimed is:

1. A method for treating and reducing a population of one or more intestinal helminths selected from the group consisting of Nematodes selected from the group consisting of: *Trichinella spiralis, Enterobius vermicularis, Ascaris lumbricoides, Trichuris trichiura, Capillaria philippinensis, Ancylcolostoma duodenale, Necator americanus*; trematodes; cestodes and combinations thereof, in a human or lower animal subject having a gastrointestinal disorder caused by helminths, by administering to the subject from about 50 milligrams to about 5000 milligrams of bismuth, per day, for about 1 to 56 days and from about 100 milligrams to about 10,000 milligrams of each of one or more antimicrobials, per day, for about 1 to about 28 days.

2. The method of claim 1 wherein the intestinal helminths are selected from the group consisting of *Enterobius vermicularis, Ancylostoma duodenale, Trichuris trichiura, Fasciolopsis buski, Taenia saginata*, and combinations thereof.

3. The method of claim 1 wherein the bismuth is administered at a level of from about 50 milligrams to about 2500 milligrams, per day.

4. The method of claim 3 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

5. The method of claim 1 wherein the antimicrobial is selected from the group consisting of penicillin, tetracycline, metronidazole, doxycycline, mebendazole, thiobendazole, praziquantel, niclosamide, ampicillin, nitrofurantoin, and atovaquone.

6. The method of claim 1 wherein the bismuth is administered for about 2 to about 28 days and antimicrobial is administered for about 1 to about 21 days.

7. A method of preventing a helminthic infection caused or mediated by one or more intestial helminths selected from the group consisting of Nematodes selected from the group consisting of: *Trichinella spiralis, Enterobius vermicularis, Ascaris lumbricoides, Trichuris trichiura, Capillaria philippinensis, Ancylcolostoma duodenale, Necator americanus*; trematodes; cestodes and combinations thereof, in a human or lower animal subject by administering to the subject from about 50 milligrams to about 5000 milligrams of bismuth, per day, for about 1 to about 21 days and from about 100 milligrams to about 10,000 milligrams of each of one or more antimicrobials, per day, for about 1 to about 14 days.

8. The method of claim 7 wherein the intestinal helminths are selected from the group consisting of *Enterobius vermicularis, Ancylostoma duodenale, Trichuris trichiura, Fasciolopsis buski, Taenia saginata*, and combinations thereof.

9. The method of claim 7 wherein the bismuth is administered at a level of from about 50 milligrams to about 2500 milligrams, per day.

10. The method of claim 9 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

11. The method of claim 7 wherein the antimicrobial is selected from the group consisting of penicillin, tetracycline, metronidazole, doxycycline, mebendazole, thiobendazole, praziquantel, niclosamide, ampicillin, nitrofurantoin, and atovaquone.

12. The method of claim 7 wherein the bismuth is administered for about 1 to about 14 days and the antimicrobial is administered for about 1 to about 7 to 10 days.

13. The method of claim 1 wherein the subject is administered a composition comprising:

(a) a safe and effective amount of bismuth;

(b) a safe and effective amount of one or more antimicrobials;

(c) pharmaceutically-acceptable carriers materials; and wherein the safe and effective amount of the bismuth and one or more antimicrobials is effective for reducing the population of the helminths.

14. The method of claim 7 wherein the subject is administered a composition comprising:

(a) a safe and effective amount of bismuth;

(b) a safe and effective amount of one or more antimicrobials;

(c) pharmaceutically-acceptable carriers materials; and wherein the safe and effective amount of the bismuth and one or more antimicrobials is effective for reducing the population of the helminths.

* * * * *